US011393579B2

(12) United States Patent
Kumar et al.

(10) Patent No.: US 11,393,579 B2
(45) Date of Patent: Jul. 19, 2022

(54) METHODS AND SYSTEMS FOR WORKFLOW MANAGEMENT

(71) Applicant: GE Precision Healthcare LLC, Milwaukee, WI (US)

(72) Inventors: Shashi Kumar, Bangalore (IN); Avinash Jha, Bhopal (IN); Chiranjeevi Ramanatha, Arkalgud Taluk (IN)

(73) Assignee: GE Precision Healthcare, Milwaukee, WI (US)

( * ) Notice: Subject to any disclaimer, the term of this patent is extended or adjusted under 35 U.S.C. 154(b) by 116 days.

(21) Appl. No.: 16/522,554

(22) Filed: Jul. 25, 2019

(65) Prior Publication Data

US 2021/0027883 A1 Jan. 28, 2021

(51) Int. Cl.
| | |
|---|---|
| *G16H 40/20* | (2018.01) |
| *G16H 30/20* | (2018.01) |
| *G16H 50/70* | (2018.01) |
| *G06Q 10/06* | (2012.01) |

(52) U.S. Cl.
CPC ......... *G16H 40/20* (2018.01); *G06Q 10/0633* (2013.01); *G16H 30/20* (2018.01); *G16H 50/70* (2018.01)

(58) Field of Classification Search
CPC ... G06F 1/00–2221/2153; G16H 10/00–80/00; G06Q 10/00–2250/905
See application file for complete search history.

(56) References Cited

U.S. PATENT DOCUMENTS

| | | | |
|---|---|---|---|
| 6,275,869 B1 * | 8/2001 | Sieffert | H04L 29/06 719/321 |
| 6,381,576 B1 | 4/2002 | Gilbert | |
| 6,674,449 B1 * | 1/2004 | Banks | A61B 6/566 715/740 |
| 6,678,669 B2 | 1/2004 | Lapointe et al. | |
| 6,955,433 B1 | 10/2005 | Wooley et al. | |
| 7,244,230 B2 | 7/2007 | Duggirala et al. | |
| 7,418,119 B2 | 8/2008 | Leichter et al. | |
| 7,458,936 B2 | 12/2008 | Zhou et al. | |
| 8,117,549 B2 * | 2/2012 | Reiner | G06Q 10/0633 715/751 |
| 8,520,978 B2 | 8/2013 | Jakobovits | |

(Continued)

FOREIGN PATENT DOCUMENTS

WO  WO-2015124192 A1 *  8/2015  ............. G16H 30/20

OTHER PUBLICATIONS

Choy et al, "Current Applications and Future Impact of Machine Learning in Radiology," Radiology: vol. 288: No. 2—Aug. 2018. (Year: 2018).*

*Primary Examiner* — Jason B Dunham
*Assistant Examiner* — Jonathon A. Szumny

(57) ABSTRACT

Various methods and systems are provided for generating an optimized workflow and assisting in clinical decision making during analysis of a patient image by a user at a site. In an example, a method includes automatically identifying one or more exam parameters associated with a diagnostic exam that includes one or more medical images and automatically generating a workflow for analyzing the one or more medical images, the workflow including one or more of a diagnostic protocol, a toolset, a prior imaging scan, a prior finding, and a reference image, the workflow generated based on the one or more exam parameters.

16 Claims, 10 Drawing Sheets

(56) References Cited

U.S. PATENT DOCUMENTS

| | | |
|---|---|---|
| 8,538,770 B2 | 9/2013 | Papier et al. |
| 8,712,798 B2 | 4/2014 | Gotman et al. |
| 9,152,760 B2 | 10/2015 | Sherman et al. |
| 2006/0242143 A1* | 10/2006 | Esham .................. G16H 30/40 |
| 2009/0129644 A1* | 5/2009 | Daw ..................... G16H 40/20 382/128 |
| 2010/0023857 A1* | 1/2010 | Mahesh ................. G06F 3/016 715/701 |
| 2010/0049740 A1* | 2/2010 | Iwase .................... G06F 19/00 705/7.27 |
| 2010/0082365 A1* | 4/2010 | Noordvyk .............. G16H 30/40 705/2 |
| 2013/0129165 A1 | 5/2013 | Dekel et al. |
| 2013/0129198 A1* | 5/2013 | Sherman ............... G16H 30/20 382/159 |
| 2013/0293481 A1* | 11/2013 | You ...................... G06F 3/0482 345/173 |
| 2014/0006926 A1 | 1/2014 | Yeluri et al. |
| 2015/0205917 A1* | 7/2015 | Mabotuwana ......... G16H 30/40 382/128 |
| 2016/0364543 A1* | 12/2016 | Dupps, Jr. ............. G16H 50/50 |
| 2017/0177812 A1* | 6/2017 | Sjolund ................. G06N 20/00 |
| 2017/0344235 A1* | 11/2017 | Sekiguchi ............. G06F 3/0484 |
| 2018/0304097 A1* | 10/2018 | Bokrantz ............... A61N 5/1031 |
| 2018/0364879 A1 | 12/2018 | Adam et al. |
| 2020/0411150 A1* | 12/2020 | Saalbach .............. G06K 9/6267 |
| 2021/0401456 A1* | 12/2021 | Cox ...................... A61B 5/339 |

\* cited by examiner

METHODS AND SYSTEMS FOR WORKFLOW MANAGEMENT

FIELD

Embodiments of the subject matter disclosed herein relate to management of workflow in healthcare and diagnostic protocols.

BACKGROUND

Healthcare environments, such as hospitals or clinics, include storage systems for storing data collected during patient procedures. The information stored therein may include, for example, patient medical histories, imaging data, test results, diagnosis information, management information, and/or scheduling information. The information may be centrally stored and accessible from a plurality of local and remote locations. Healthcare workflow may include retrieval and analysis of patient data, such as prior patient scans stored on a picture archiving and communication systems ("PACS"), from the storage systems for analysis by a healthcare practitioner. For example, a radiologist may retrieve earlier scans for comparison with a current scan. The healthcare workflow may also dictate that the practitioner identify relevant literature references and relevant prior diagnosed cases for comparison with the patient's current scan to make a reliable diagnosis.

BRIEF DESCRIPTION

In one embodiment, a method includes automatically identifying one or more exam parameters associated with a diagnostic exam that includes one or more medical images and automatically generating a workflow for analyzing the one or more medical images, the workflow including one or more of a diagnostic protocol, a toolset, a prior imaging scan, a prior finding, and a reference image, wherein the workflow is generated based on the one or more exam parameters. In this way, user fatigue and error in workflow selection may be reduced, while improving productivity and efficiency in diagnostic outcomes.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
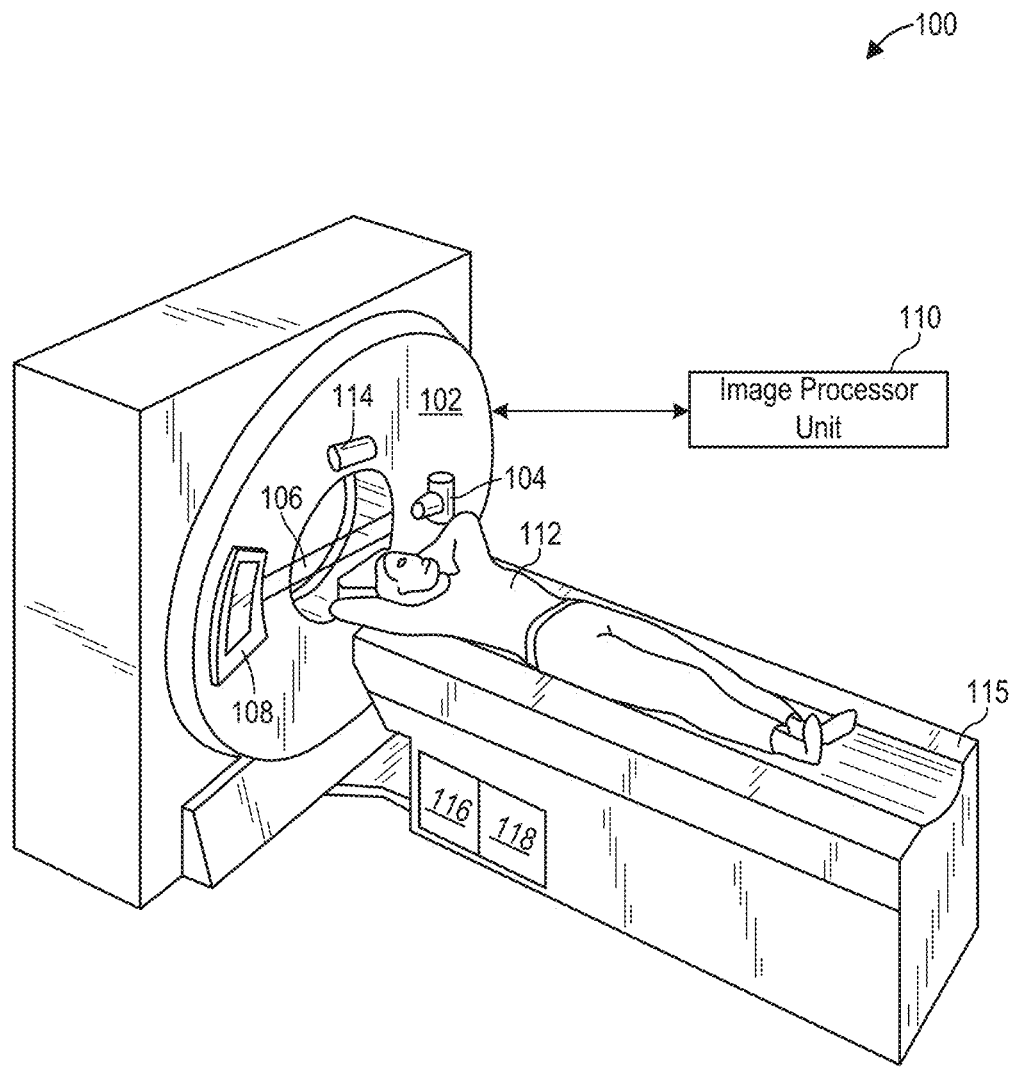
FIG. 1 shows a pictorial view of an imaging system according to an embodiment.

The following description relates to various embodiments of workflow management including protocol management and clinical decision support systems. In particular, systems and methods are provided for enabling a clinician to be provided with a workflow that allows for easier and improved analysis of images acquired during a diagnostic imaging scan and a more reliable diagnosis of a suspected condition.

Following acquisition of patient imaging data on an imaging system, a clinician, such as a radiologist, may perform an analysis of the acquired images, in what is referred to as an exam or study. Therein, the clinician may diagnose or rule out a suspected condition based at least in part on the images acquired in the current scan. The analysis may include comparing the images acquired in the current patient scan to one or more earlier scans of the same patient, reference images, reference literature, and so forth. However, the clinician has to select which of the earlier scans to compare the current scan to. In addition, the clinician has to determine an order in which to view the scans so as to best arrive at a diagnosis. The clinician may also have to identify and retrieve reference literature and images pertaining to the condition being diagnosed. For example, the clinician may have to identify scans from confirmed cases including confirmed cases from other patients at the same healthcare facility or patients at an alternate facility, confirmed cases from published literature, landmark confirmed cases from reference books, reference images that show normal anatomical features, etc. During the exam, the clinician may also need to retrieve clinical data pertaining to the patient at the time of the scan (e.g., blood test results, body temperature readings, blood pressure readings, etc.). These may need to be taken into account during the diagnosis. Further still, to analyze the images, the clinician may have to select one or more toolsets. The one or more toolsets may include user interface menu options/control buttons that, when selected, allow certain tasks to be performed, such as window-leveling, pan, zoom, application of image analysis functions, etc. The toolset selection may be based on the imaging modality but also based on the suspected condition being diagnosed, user preferences, etc. For example, there may be a specific toolset that is recommended to be used at the given healthcare facility when analyzing mammograms. Additionally or alternatively, there may be a specific toolset (e.g., zoom, pan, rotate, slice, etc.) that the given clinician finds useful when analyzing mammograms, based on the clinician's history of mammogram analyses. In some examples, once the clinician has performed the exam to arrive at a diagnosed condition, the exam may be further reviewed by another clinician, such as a doctor specializing in treating the diagnosed condition, before a final diagnostic result is delivered to the patient.

As described above, at the time of image analysis, there can be a significant cognitive load on the clinician. If any of the above-mentioned parameters are altered, the diagnosis may be affected. For example, if the clinician does not select the correct reference image for comparison (e.g., wrong size, wrong orientation, wrong condition, wrong body part, etc.), then an underlying condition may be go undiagnosed. As another example, if the clinician does not select the correct set of previous patient scans, or does not analyze the previous patient scans in a particular order, the suspected condition may be misdiagnosed. If the clinician is tired or fatigued, there is a greater possibility of an incorrect selection being made, and diagnostic accuracy being affected.

Thus, according to embodiments disclosed herein, a guided diagnostic workflow may be automatically generated when a clinician is performing an exam that includes analyzing diagnostic medical images of a patient, reducing the cognitive load on the clinician. Upon storage and/or retrieval of a new exam of a patient, a computing system may automatically, and without user input, detect and identify various parameters related to the exam. These may include, for example, parameters relating to the identity of the patient, the imaging modality used to acquire the patient images that are to be analyzed in the exam, a suspected patient condition, etc. Following the automatic detection of the various parameters, the computing system may automatically generate a diagnostic workflow. Therein, based on the identified parameters, the computing system may automatically select and retrieve relevant earlier patient scans, as well as reference images and literature results that are most pertinent for the current exam. The computing system may be configured to use artificial intelligence-based models to identify, retrieve, and display prior data that can assist the clinician in diagnosing the suspected condition, thereby reducing the cognitive load on the clinician while also improving the diagnostic efficiency. In addition to identifying the relevant prior scans and references, the diagnostic workflow may also populate the display with a toolset that is most suited for the current exam, based on the suspected patient condition, imaging modality, and/or clinician. Further, the prior scans and references may be displayed in accordance with a hanging protocol selected corresponding to the selected diagnostic workflow.

Further, the computing system may include a database of diagnostic workflows and may select a workflow from the database based on diagnostic accuracy that is learned iteratively. For example, a clinician may execute a workflow for an exam of a patient scan using a particular hanging protocol, a particular toolset, a particular set of reference images, a particular set of prior patient scans, etc. Details of the workflow are saved in the database. The clinician may make an initial diagnosis based on the images in the patient scan, clinical information about the patient, the prior scans, etc., analyzed according to the executed workflow. The initial diagnosis may be stored in the database along with the details of the workflow. Further, in some examples, corroboration of the initial diagnosis, if made, may also be stored in the database. The corroboration may include a diagnosis made by another clinician upon viewing the exam, additional information from follow-up procedures performed on the patient, etc. If the initial diagnosis is corroborated, then the associated workflow may be assigned a higher score indicating that the workflow enabled the clinician to reliably identify the suspected condition. If the initial diagnosis is not corroborated or if the other clinicians or procedures indicate a condition other than made in the initial diagnosis, then the associated workflow may be assigned a lower score indicating that the workflow did not enable the clinician to reliably identify the suspected condition. Scores may be assigned based on diagnostic efficiency as well as user modifications to the workflow (e.g., if a user modified the workflow extensively, the score may be lower than for a workflow where a user did not make any modifications), amount of time to diagnosis, or other factors that may indicate the efficiency and/or usefulness of the workflow. If a workflow has a higher than threshold score, indicative of a workflow with a high diagnostic reliability and/or efficiency, the workflow may be stored in the workflow database as a function of various workflow parameters including the patient identity, the diagnosed condition, the imaging modality, the clinician identity, etc. At a later time, the workflow may be provided as an option to the same clinician, or an alternate clinician, when analysis of another scan of the same modality, condition, and/or patient is being performed. This allows reliable workflows to be shared.

Figure 2:
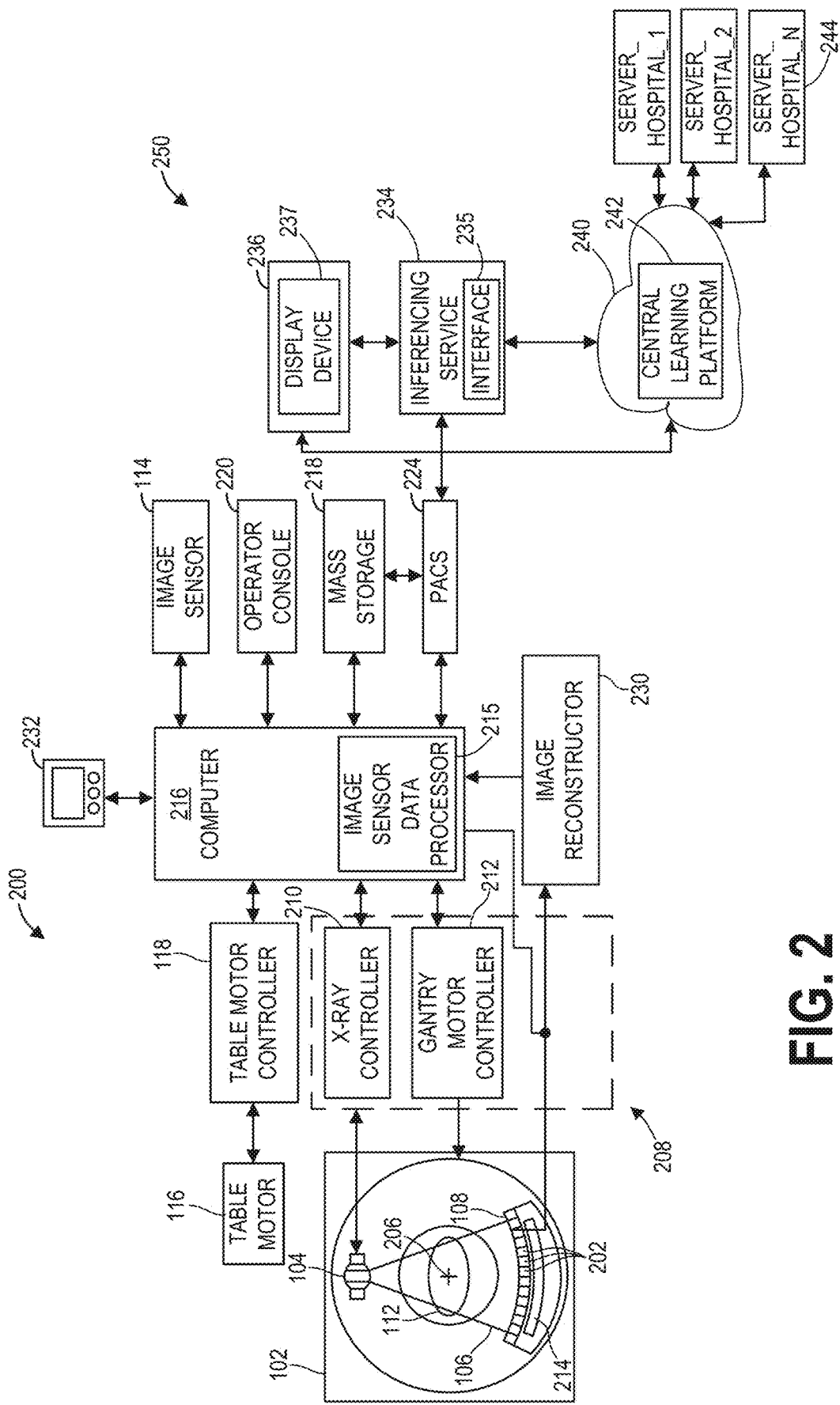
FIG. 2 shows a block schematic diagram of an exemplary imaging system according to an embodiment.
Figure 3:
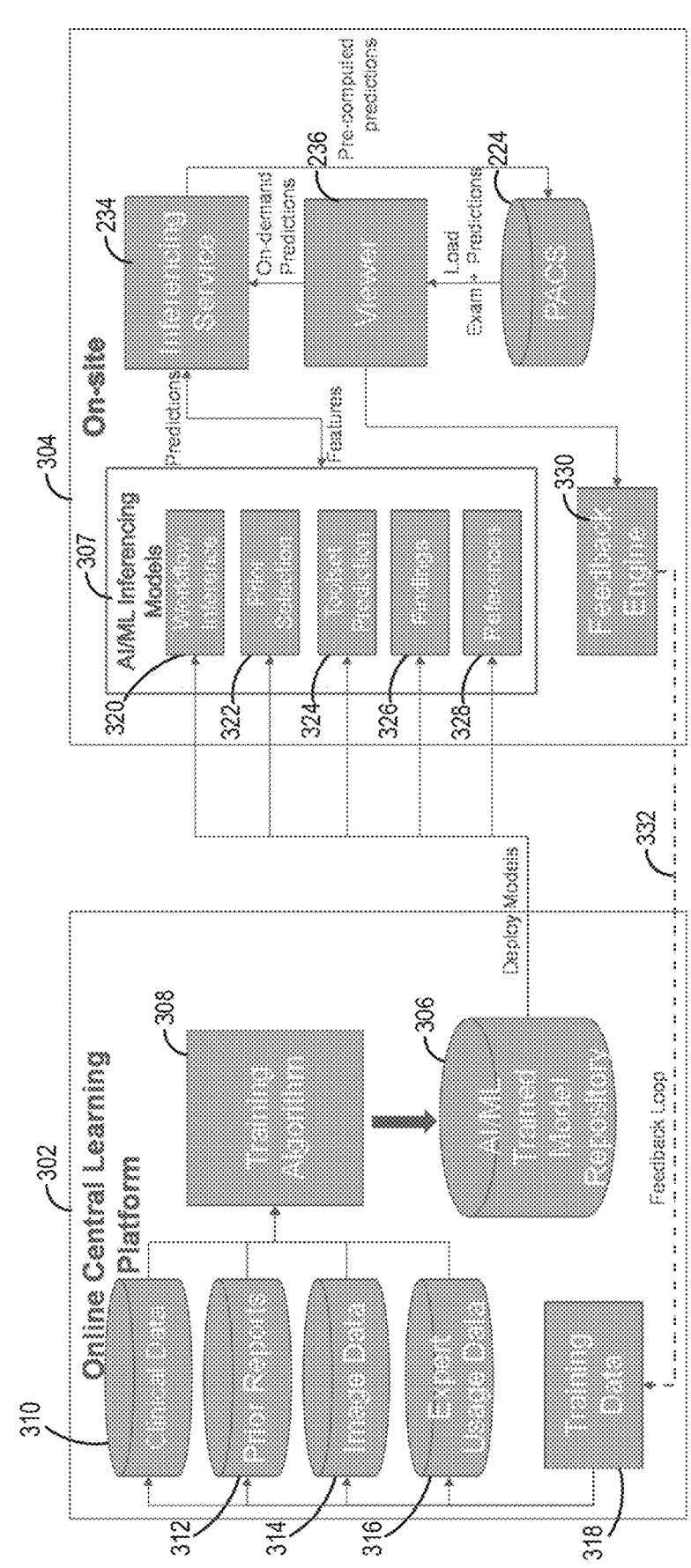
FIG. 3 shows an example embodiment of an online central learning platform that is coupled to a healthcare system PACS.
Figure 4:
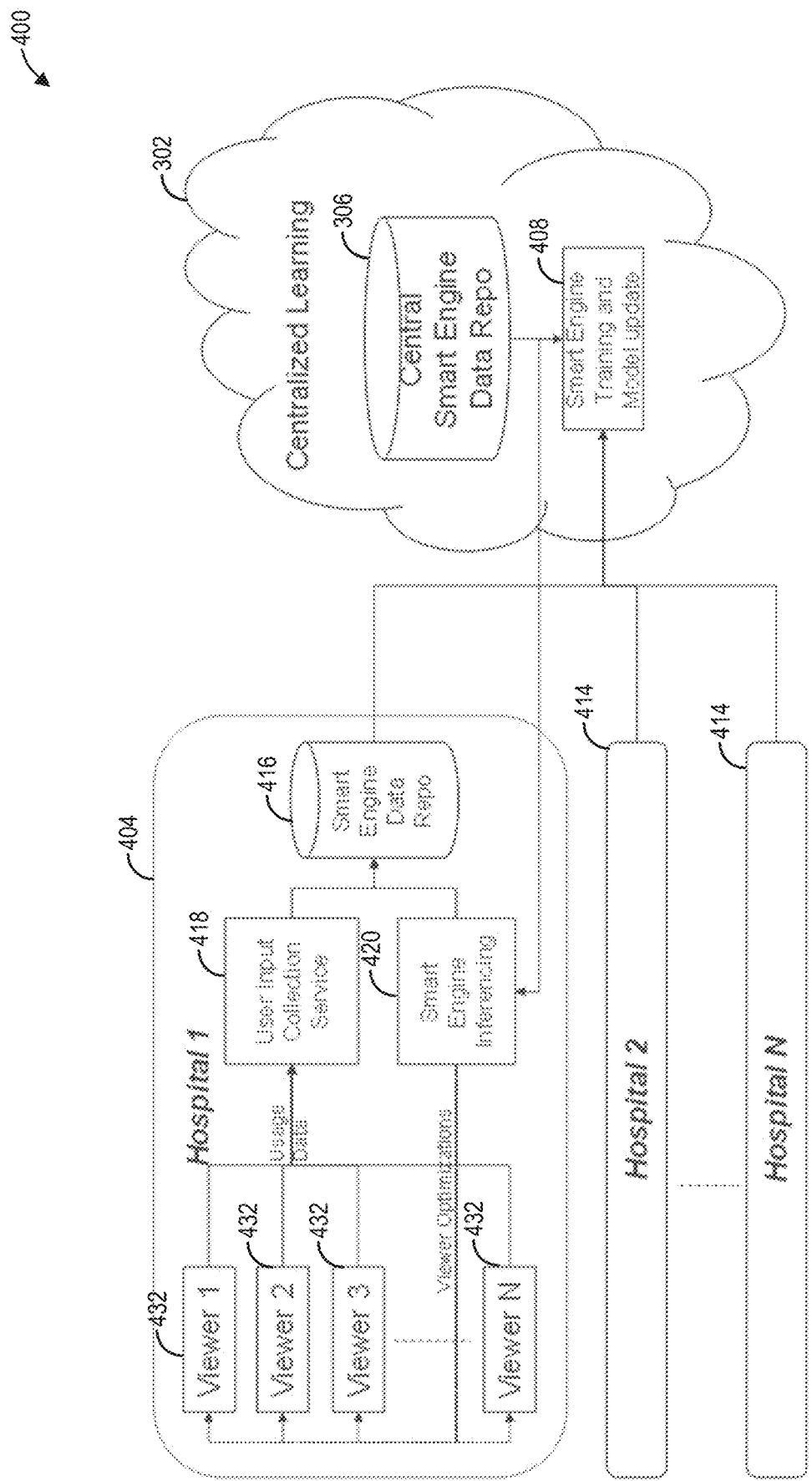
FIG. 4 shows an example embodiment of the online central learning platform of FIG. 3 integrated with a plurality of healthcare environments.
Figure 5:
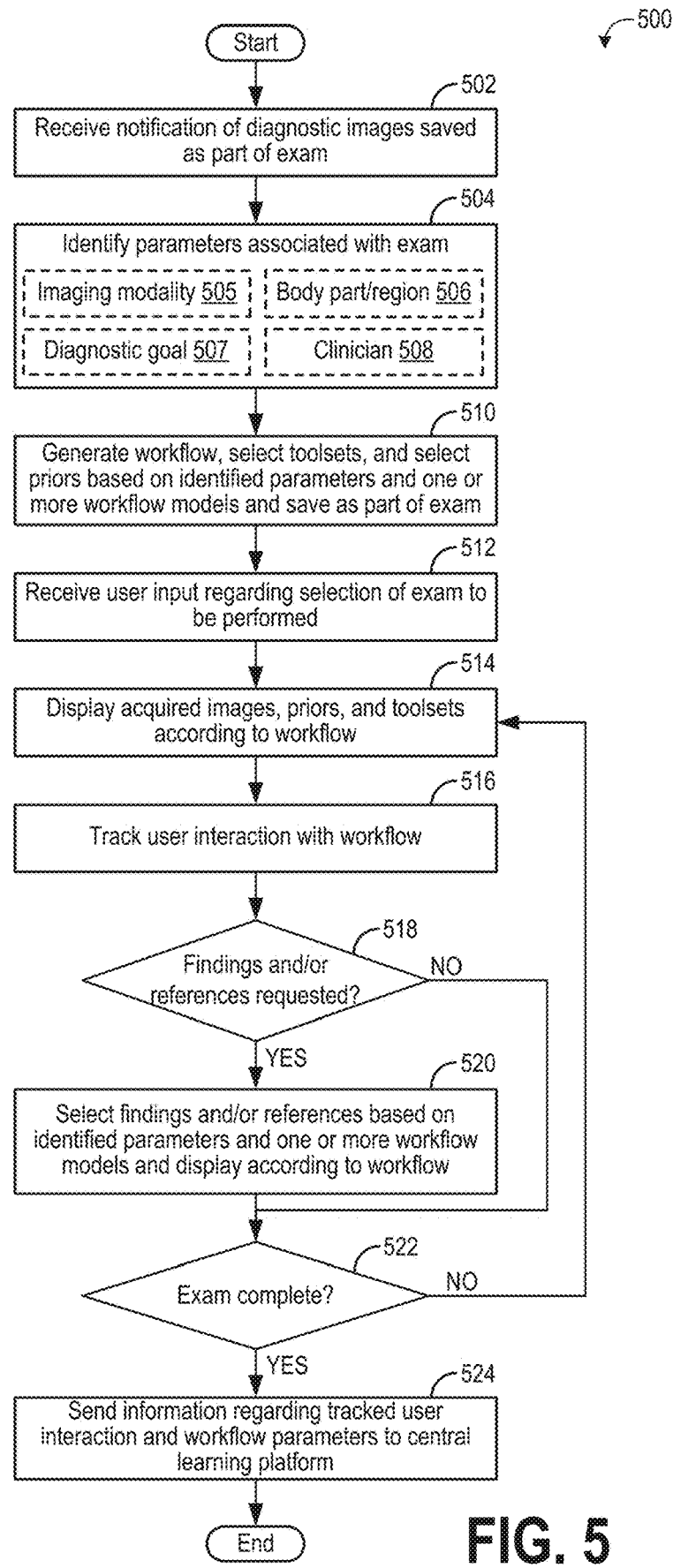
FIG. 5 shows an example method for automatically generating a workflow for a diagnostic exam based on output from one or more workflow models.
Figure 6:
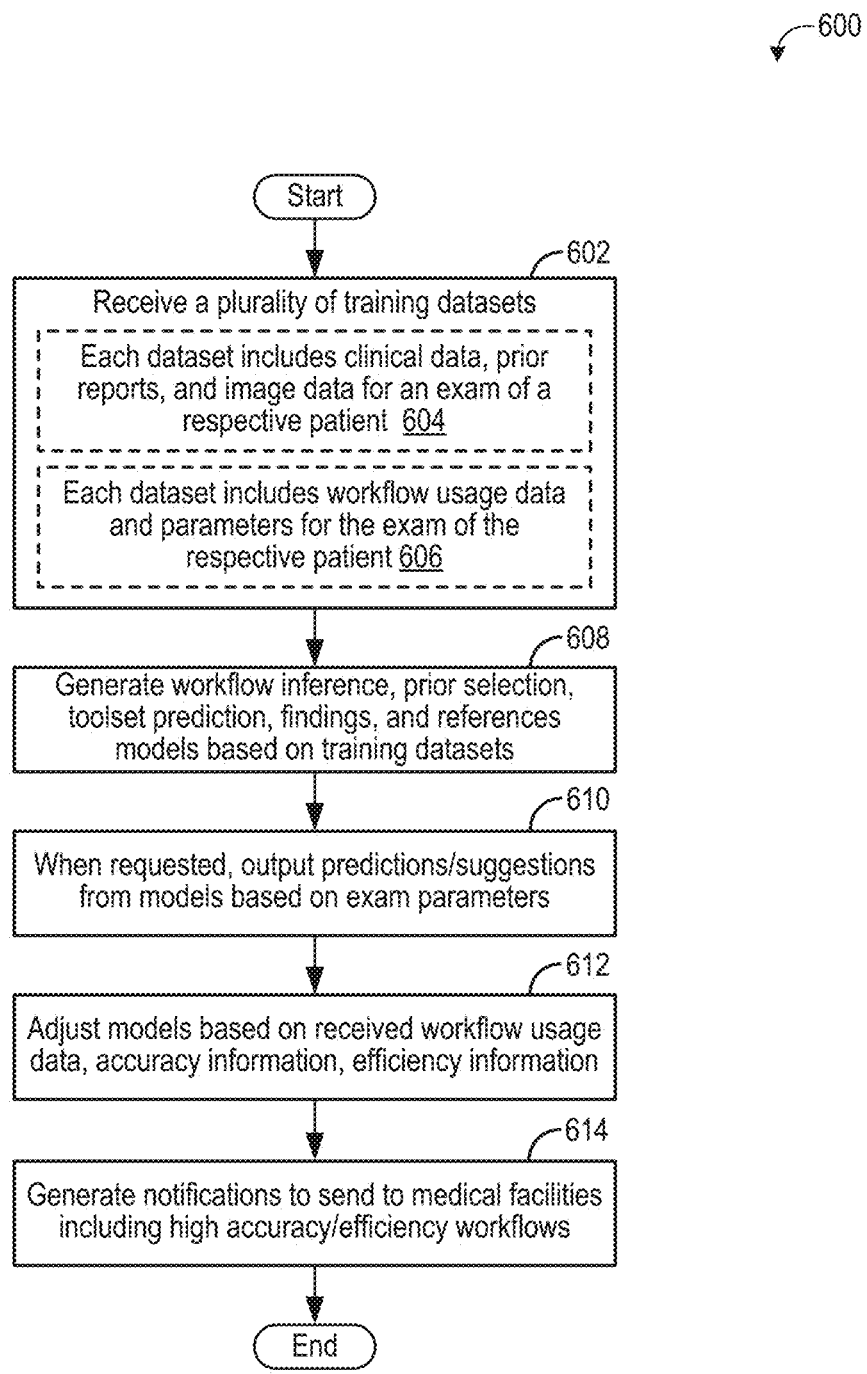
FIG. 6 shows an example method for training the one or more workflow models.
Figure 7:
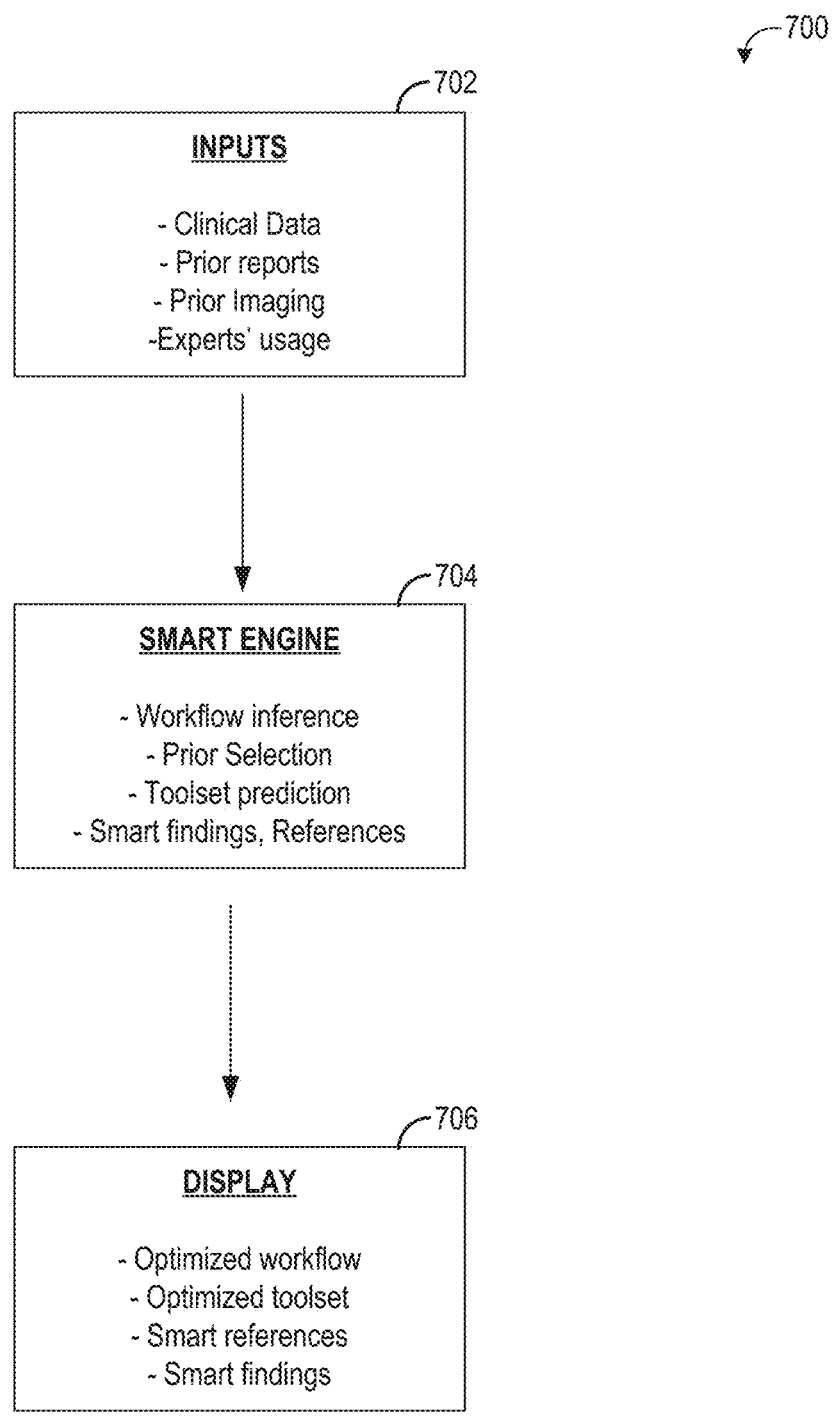
FIG. 7 shows an example overview of training and execution of the one or more workflow models.
Figure 8:
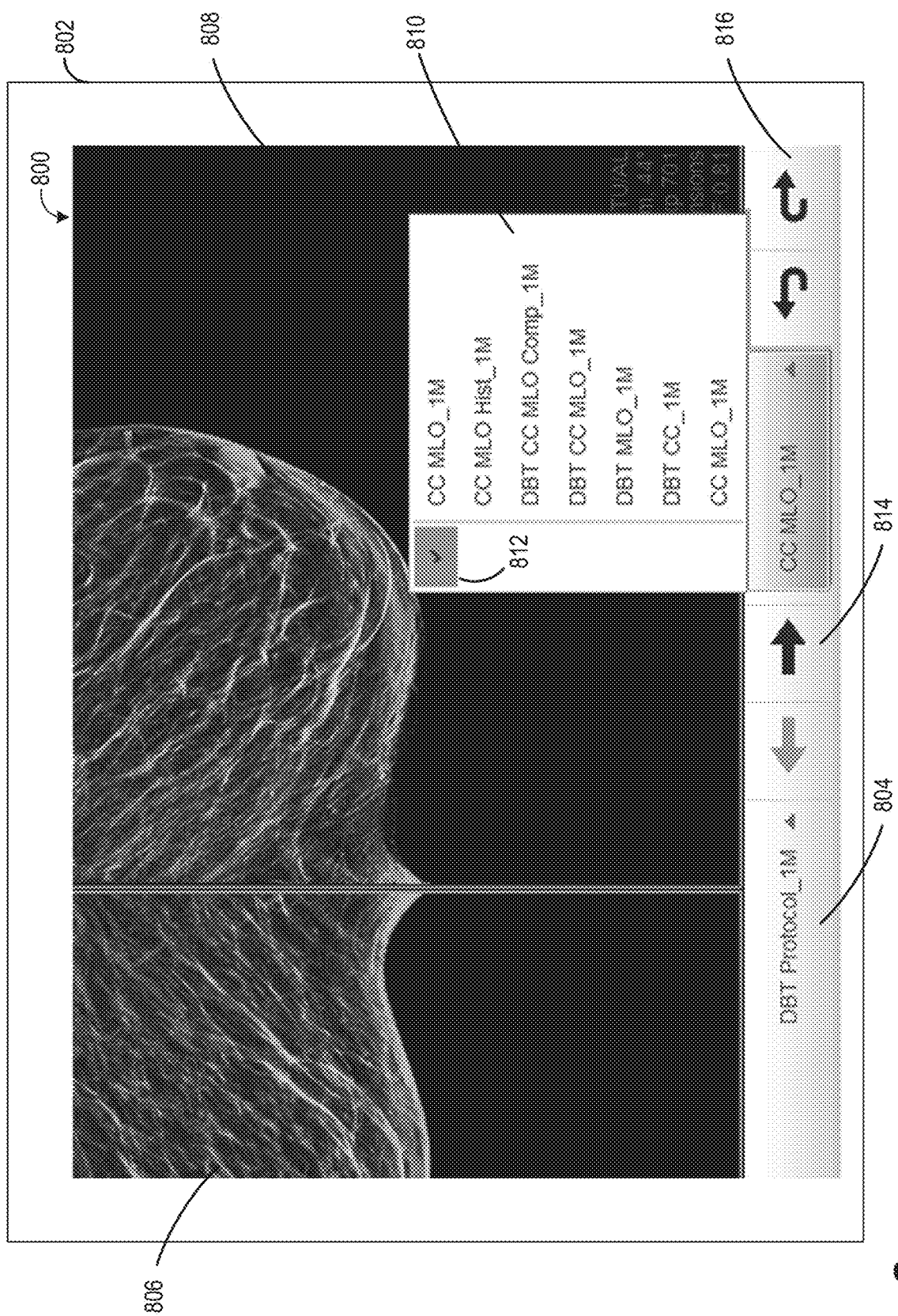
FIG. 8 shows an example workflow interface displaying options associated with an optimized workflow.
Figure 9:
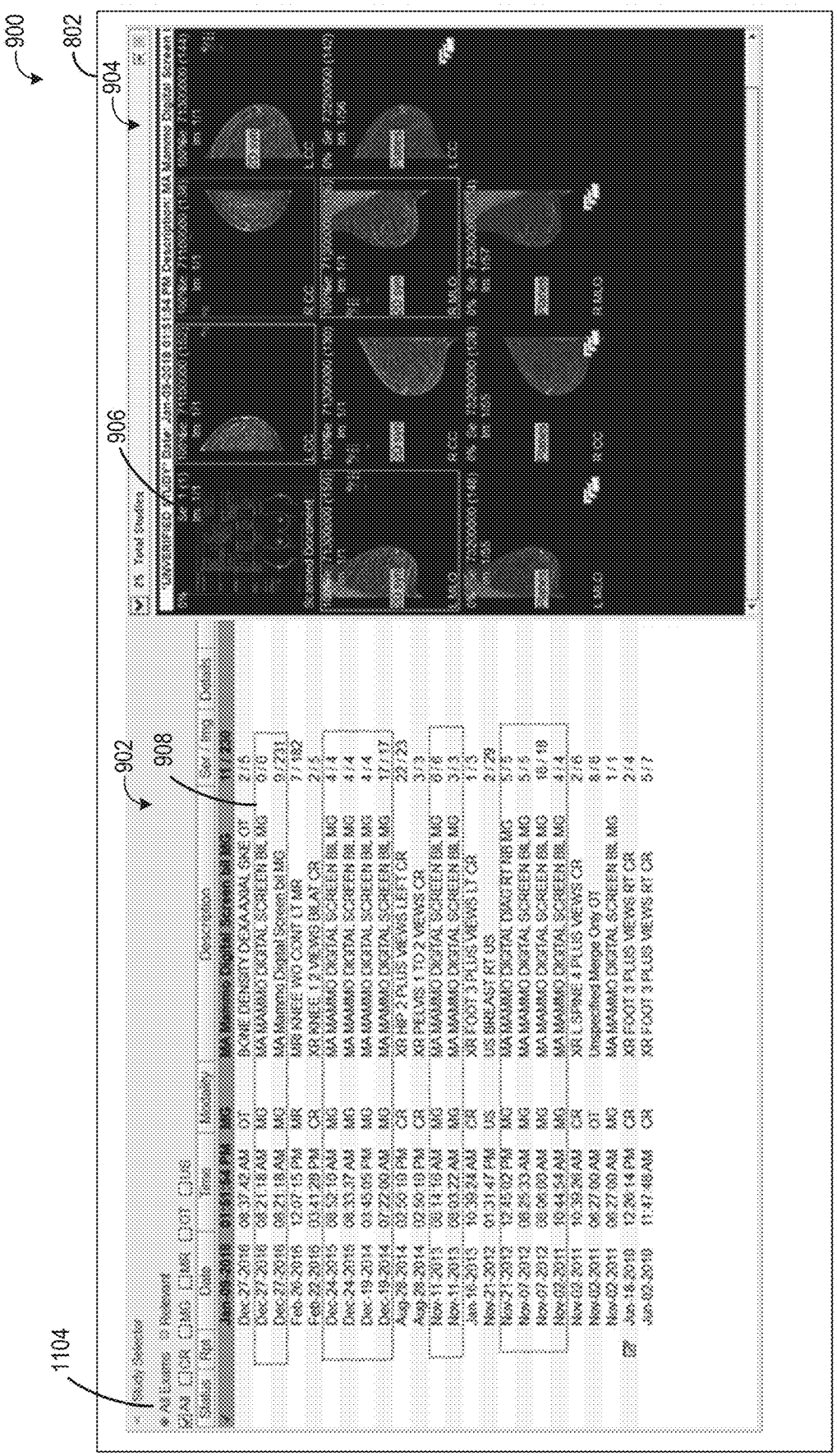
FIG. 9 shows an example interface displaying selected patient image priors in accordance with an optimized workflow.
Figure 10:
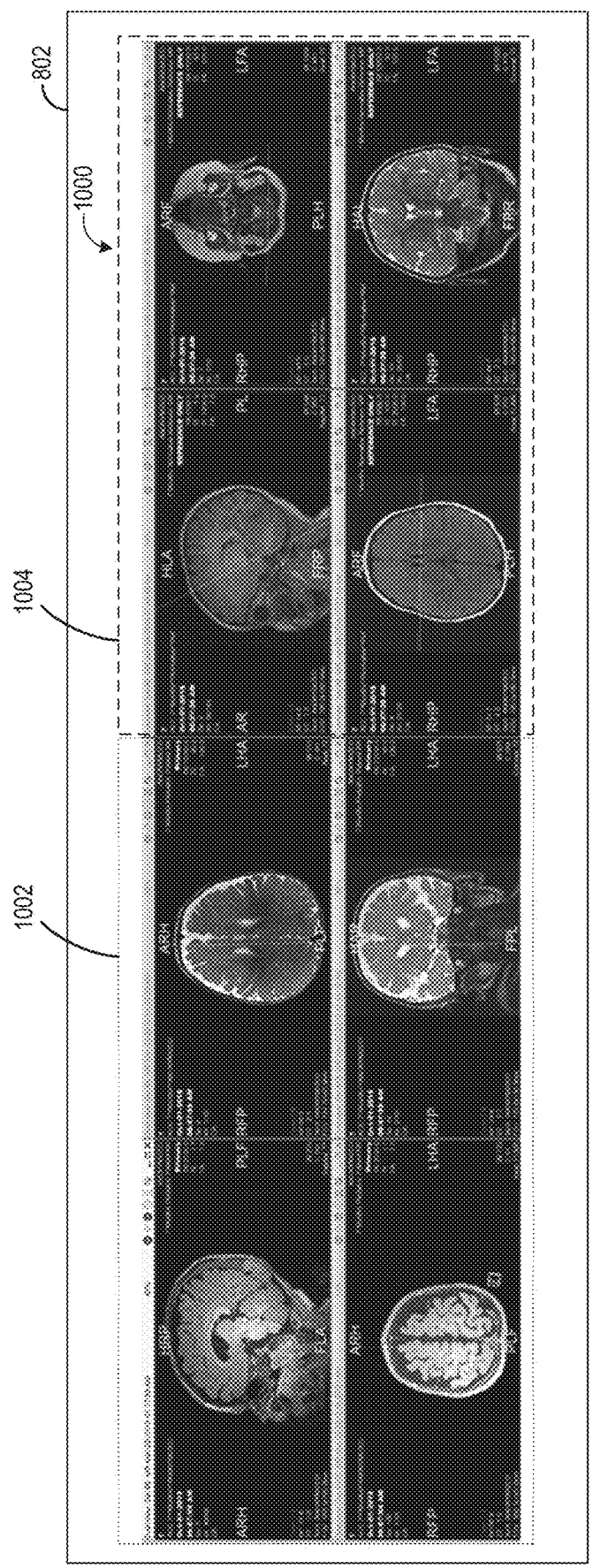
FIG. 10 shows an example interface displaying selected reference images in accordance with an optimized workflow.

An example medical imaging system in the form of a CT imaging system that may be used by a scan technologist to acquire images of a patient is provided in FIG. 1. The imaging system may be communicatively coupled to a PACS system, as shown at FIG. 2, for storing the images acquired with the imaging system, and the PACS may be coupled to a inferencing service for assisting in workflow generation during a diagnostic exam that includes analysis of the acquired images by a clinician. FIG. 3 shows an example embodiment of a central learning platform that is coupled to a healthcare system PACS and inferencing service for generation of a workflow when a user retrieves a scan for diagnostic analysis (e.g., execution of the exam). FIG. 4 shows the central learning platform integrated with the healthcare system of multiple different healthcare environments, such as different hospitals, so that workflows generating reliable diagnostic outcomes may be shared among the different hospitals. FIG. 5 shows a flow chart for automatically generating and applying a diagnostic workflow during a diagnostic exam of medical images based on the output from one or more workflow models. FIG. 6 shows a method for training the one or more workflow models via a central learning platform. FIG. 7 shows an example flow of data through a smart engine of the central learning platform, the engine receiving data inputs from various sources and facilitating display of selected data on a display as part of an optimized workflow. FIG. 8 shows an example optimized workflow that may be displayed to a user. FIG. 9 shows a workflow interface wherein relevant priors (e.g., relevant imaging scans and/or reports) are automatically identified. FIG. 10 shows a workflow interface wherein relevant reference images are automatically selected and loaded for display to a user.

Though a CT system is described by way of example, it should be understood that the present techniques may also be useful when applied to imaging sessions with other imaging modalities, such as a positron emission tomography imaging system, a nuclear medicine imaging system, a magnetic resonance imaging system, an x-ray radiography imaging system, an x-ray fluoroscopy imaging system, an interventional imaging system (e.g., angiography, biopsy), an ultrasound imaging system, and so forth. The present discussion of a CT imaging modality is provided merely as an example of one suitable imaging modality.

FIG. 1 shows example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. Throughout the disclosure, the terms subject and patient may be used interchangeably, and it is to be understood that a patient is one type of subject that may be imaged by the CT system, and that a subject may include a patient, at least in some examples. In one embodiment, the CT system 100 includes a gantry 102, which in turn may further include at least one x-ray radiation source 104 configured to project a beam of x-ray radiation 106 for use in imaging the patient. Specifically, the radiation source 104 is configured to project the x-rays 106 toward a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In some examples, CT system 100 may include an imaging sensor 114 positioned on or outside the gantry 102. As shown, the imaging sensor 114 is positioned on an external side of the gantry 102 and orientated to image the subject 112 when the subject is at least partially outside the gantry 102. The imaging sensor 114 may include a visible light sensor and/or and an infrared (IR) sensor that includes an IR light source. The IR sensor may be a three-dimensional depth sensor such as a time-of-flight (TOF), stereo, or structured light depth sensor operable to generate three-dimensional depth images, while in other implementations the infrared sensor may be a two-dimensional IR sensor operable to generate two-dimensional IR images. In some implementations, a two-dimensional IR sensor may be used to infer depth from knowledge of IR reflection phenomena to estimate three-dimensional depth. Whether the IR sensor is a three-dimensional depth sensor or a two-dimensional IR sensor, the IR sensor may be configured to output a signal encoding an IR image to a suitable IR interface, which may be configured to receive the signal encoding the IR image from the IR sensor. In other examples, the imaging sensor may further include other components, such as a microphone to enable the reception and analysis of directional and/or non-directional sounds coming from an observed subject and/or other sources.

In certain embodiments, the CT system 100 further includes an image processing unit 110 configured to reconstruct images of a target volume of the patient using a suitable reconstruction method, such as an iterative or analytic image reconstruction method. For example, the image processing unit 110 may use an analytic image reconstruction approach such as filtered back-projection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), and model-based iterative reconstruction (MBIR), and so on to reconstruct images of a target volume of the patient.

CT system 100 further includes a table 115 on which a subject to be imaged may be positioned. The table 115 may be motorized so that the vertical and/or lateral position of the table may be adjusted. Accordingly, table 115 may include a motor 116 and a motor controller 118. The table motor controller 118 moves the table 115 by adjusting the motor 116 for appropriately positioning the subject in the gantry 102 for acquiring projection data corresponding to the target volume of the subject. Table motor controller 118 may adjust both the elevation of table 115 (e.g., the vertical position relative to a ground on which the table sits) and lateral position of table 115 (e.g., the horizontal position of the table along an axis parallel to a rotational axis of the gantry).

FIG. 2 illustrates an exemplary imaging system 200 similar to the CT system 100 of FIG. 1. In one embodiment, the system 200 includes the detector array 108 (see FIG. 1). The detector array 108 further includes a plurality of detector elements 202 that together collect the x-ray beams 106 (see FIG. 1) that pass through the subject 112 to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 112 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device (or computer) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device. The storage device may be internal or external to computing device 216. In still further examples, the data may be transmitted by the computing device to a cloud-based server for storage. While only a single computing device 216 is illustrated in FIG. 2, in some examples computing device 216 may be distributed across multiple physical devices.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In some embodiments, the system 200 either includes or is coupled to a picture archiving and communications system (PACS) 224. In an exemplary implementation, the PACS 224 is further coupled to one or more other storage systems such as a radiology department information system, hospital information system, and/or to an internal or external network (not shown) to allow users at different locations (e.g., within the same medical facility as the imaging system and/or at different medical facilities) to gain access to the image data.

As described further herein, the computing device 216 uses the operator-supplied and/or system-defined commands and parameters to operate the table motor controller 118, which in turn, may control the motorized table 115. For example, the computing device 216 may send commands to the motor controller 118 instructing the motor controller 118 to adjust the vertical and/or lateral position of the table 115 via the motor 116.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In some examples, the computing device 216 may include computer-readable instructions executable to send commands and/or control parameters to one or more of the DAS 214, the x-ray controller 210, the gantry motor controller 212, and the table motor controller 226 according to an imaging protocol. Further, the computing device 216 may set and/or adjust various scan parameters (e.g., dose, angle of gantry rotation, kV, mA, attenuation filters) according to the imaging protocol. The imaging protocol may be selected by the operator from among a plurality of imaging protocols stored in memory on the computing device 216 and/or a remote computing device, or the imaging protocol may be selected automatically by the computing device 216 according to received patient information, for example.

Additionally, in some examples, computing device 216 may include an image sensor data processor 215 that includes instructions for processing imaging information received from an imaging sensor, such as sensor 114 of FIG. 1. The information received from the imaging sensor, which may include depth information and/or visible light information, may be processed to determine various subject parameters, such as subject identity, subject size, current subject position, subject movement, etc. These subject parameters may be used by the computing device 216 or another suitable device to adjust various parameters of the medical imaging session, such as pausing image acquisition and/or outputting notifications to the subject and/or operator when subject movement is detected. Further, video stream(s) from the imaging sensor may be displayed via display 232.

The information from the image sensor may be usable by the image sensor data processor 215 to perform tracking of one or more subjects in the field of view of the image sensor. In one example, the image information (e.g., depth information) may be used to perform skeletal tracking, wherein a plurality of joints of the subject are identified and analyzed to determine movement, pose, position, etc., of the subject.

The location of the joints during skeletal tracking may be used to determine the subject parameters described above.

The imaging system of FIGS. 1-2 may be operated in accordance with an imaging protocol. Computer 216 may include one or more default and/or customized imaging protocols stored in the memory (such as in mass storage 218). In one example, one or more of the imaging protocols stored in the memory may be manufacturer installed imaging protocols provided as a library of imaging protocols. The imaging protocols may be selectively configured for the associated imaging modality (such as for computerized tomography imaging, magnetic resonance imaging, positron emission tomography, etc.). The different imaging protocols may be associated with various imaging parameters, such as a medical condition being assessed for, a body part being scanned, patient characteristics, and combinations thereof. For example, a distinct imaging protocol is provided for scanning a mid-sized adult's abdomen for signs of bleeding as compared to scanning a child's head for signs of concussion, and so on. Each imaging protocol may include settings for the imaging system (e.g., imaging system 200 of FIG. 2), such as settings for the gantry motor, the x-ray, the table motor, etc.

Also shown in FIG. 2 is a diagnostic exam system 250 that may be used to perform diagnostic exams based on images acquired with imaging system 200 and/or other imaging systems. Diagnostic exam system 250 includes a viewer 236 that is communicatively coupled to PACS 224 and/or an inferencing service 234. Viewer 236 may be a computing device that includes memory, processor(s), and a display device 237, similar to computing device 216 and display 232. Likewise, inferencing service 234 comprises one or more computing devices each including memory and processor(s), similar to the memory and processors described above with respect to the computing device 216. Inferencing service 234 may generate an interface, referred to herein as a workflow interface 235, to assist a user with workflow management during a diagnostic exam of images, e.g., acquired during a scan using imaging system 200. Interface 235 may be output for display on the display device 237 during the diagnostic exam.

While inferencing service 234 is shown as being a separate device than viewer 236 and separate from (though communicatively coupled to) PACS 224, in some examples inferencing service 234 may be stored on and executed by a different computing device, such as viewer 236, computing device 216, or a computing device that is a part of PACS 224. Further, one or more additional computing devices may be coupled to PACS 224 and/or inferencing service 234 to allow users to view images saved on PACS 224 and execute diagnostic exams according to the embodiments disclosed herein.

During a diagnostic exam, inferencing service 234 may generate a workflow based on user input and/or according to artificial intelligence-based models. The workflow may include a protocol, toolsets, etc., that may be applied when a diagnostic exam of images is performed. The inferencing service 234 may generate a workflow for each diagnostic exam, and the workflows may differ such that optimized workflows for the types of images, diagnostic goal of the exam, user carrying out the exam, etc., may be generated. For example, a first workflow may be provided for an exam directed to determining if a mid-sized adult's abdomen is showing signs of bleeding. A different workflow may be provided for diagnosing a child's head for signs of concussion, and so on. Each workflow may include toolsets that are specific for the given modality and/or body region that was imaged. Further, toolsets may be customized based on user settings and preferences (such as toolsets a user uses frequently, left or right handedness of user, etc.). The workflow may also include a hanging protocol which may indicate an order of presentation of images during the exam. Via the multiple action items of the workflow, the user may perform an initial diagnostic assessment. For example, the user may analyze the images of the patient acquired during the scan to diagnose a suspected condition of the patient.

Further, the inferencing service 234 may automatically or semi-automatically (e.g., in response to user request) retrieve relevant patient clinical data, relevant prior images, relevant reference literature, and relevant reference images for display to the user on the display device 237 associated with viewer 236 as part of the workflow. The references, images, and priors identified in this way may be local data, such as data sources from a healthcare environment where the CT imaging system 200 is located. As non-limiting examples, the inferencing service 234 may retrieve earlier patient scans of the same body region as a current scan, scans of the same body region from another patient wherein the suspected condition has been confirmed, as well as reference images.

Inferencing service 234 may also be configured to retrieve data from remote sources. For example, inferencing service 234 may be communicatively coupled to a central learning platform 242. As elaborated at FIG. 3, the central learning platform 242 may be stored on a cloud network 240 and may be in communication with computing devices (e.g., servers and/or PACS) of multiple other healthcare environments, such as servers 244 of hospitals 1 through N, as well as remote services such as reference image libraries and reference literature libraries. As a result, reference images and/or reference literature be selected from any of those locations and displayed to the user at display 237 as part of an optimized workflow. Further, workflow usage data may be collected from the other healthcare environments and used to train one or more models via the central learning platform. The one or more models may be deployed to assist in generating the diagnostic workflows, as explained above and in discussed in more detail below.

As elaborated with respect to FIG. 3, the central learning platform 242 and/or inferencing service 234 may be used to generate workflow inferences, assist in selection of relevant priors, and assist in selection of toolsets, findings, and references. By enabling the relevant images, priors, and references to be automatically identified, retrieved, and displayed, the cognitive load and fatigue on the user (e.g., clinician) is reduced while also improving the diagnostic reliability of the exam. For example, misdiagnoses including diagnoses that would have otherwise not been identified, can be reduced.

Turning now to FIG. 3, an example embodiment is shown of a smart workflow system 300 that includes an online central learning platform 302 in communication with one or more on-site computing devices 304. In one example, the central learning platform 302 is provided on one or more centralized servers, such as a cloud network (see FIG. 2), so that the central learning platform 302 can be accessed by the one or more on-site computing devices 304, which may include computing device(s) at one or more healthcare environments (e.g., hospitals). Platform 302 may include resources (e.g., memory and processors) allocated to train one or more workflow models that may be deployed by the one or more on-site computing devices 304 in order to predict/provide suggestions for optimal workflow protocols, prior selections, toolset predictions, findings, references, and so forth, during execution of a diagnostic exam based on one or more diagnostic images of a patient.

The platform 302 includes a training algorithm 308 that is configured to train one or more workflow models using training data 318. The training data may include input-output pairs for each of a plurality of patients. The training data that may be included as the input segment of the input-output pairs to the training algorithm 308 include, for example, clinical data 310 (such as blood test results, blood pressure and body temperature readings, etc.), prior reports 312 (such as conditions diagnosed from prior scans or other diagnostic tests), and image data 314 (such as images from earlier scans). The output segment of the input-output pairs may include, for each patient, expert usage data 316 (such as confirmation of diagnoses made by experts, e.g., clinicians, as well as usage data related to how users of on-site computing device 304 or other devices interacted with various workflows). The algorithm uses artificial intelligence (AI), such as machine learning (ML), methods to train the one or more workflow models, which may be saved in a model repository 306. The models are then deployed at the on-site computing device 304 at an on-site location, such as a location where a clinician retrieves a scan for performing a diagnostic exam.

The workflow models include, for example, a workflow inference model 320. The workflow inference model 320 is configured to infer a workflow that is most suited for a diagnostic exam retrieved by and performed by a clinician such as a radiologist. The workflow inference model 320 may suggest/predict an order and identity of action items to be performed as part of a protocol for a diagnostic exam, which may include analysis of acquired images to diagnose a suspected condition (as a function of the condition, the body part, the imaging modality, etc.). The workflow inference model 320 may suggest/predict the viewport(s) in which the priors, toolsets, references, etc., are to be displayed, the size of the viewports, positions of the viewports, and any other aspects of the layout and visual appearance of the graphical user interface that is used to present the images and other information to the user during the diagnostic exam. Further, the workflow inference model 320 may suggest/predict a hanging protocol for the images that are to be analyzed in the current exam. As an example, if the clinician has retrieved a mammogram exam for a patient to diagnose for the presence of a tumor, the workflow inferencing model 320 may be used to suggest a workflow including a hanging order in which the currently acquired images should be viewed so as to reliably diagnose for a breast tumor. In this way, the workflow inference model may suggest a workflow to allow a user (e.g., clinician) to navigate through the process of reading the images in the exam. The models 307 may also include a prior selection model 322 that may be deployed for selection of priors including the identification and selection of prior data, prior images, etc. The prior images may include prior images collected for the current patient, as well as prior images collected from other patients at the given on-site location with confirmed diagnoses. The models 307 may also include a toolset prediction model 324 that may be deployed for the selection and display of toolsets that are determined to enable reliable diagnosis of the suspected condition, as well as toolsets selected based on user settings. For example, the toolset prediction model 324 may automatically predict and suggest toolsets that are used for mammogram analysis by the given clinician, as well as toolsets that were used during the diagnosis of confirmed prior cases. The predicted toolset may include a selected set of tools as well as a defined relative positioning of the tools. For example, if a zoom tool was used in the diagnostic workflow of most of the confirmed prior cases, the zoom tool may be suggested with a position of the zoom tool adjusted based on the handedness (e.g., left or right) of the user.

The models 307 may also include a findings model 326 that may be deployed to enable identification of relevant findings and a references model 328 that may be deployed to enable identification of relevant references (e.g., reference images, reference literature). The findings model 326 may predict or suggest, for example, relevant findings from prior exams. The findings may then be copied over into the current exam, and may be adapted based on the clinical data for the current patient, diagnostic goal of the current exam (e.g., to determine a change in size of a previously identified lesion), and so forth. The references model 328 may predict or suggest, for example, prior images of a confirmed diagnosis (e.g., confirmed presence of tumor, and confirmed absence of tumor) and/or normal reference images (e.g., images that do not include any diagnosed abnormalities). The references model 328 may also predict or suggest reference literature (e.g., images and/or abstracts from the literature) pertaining to various matters related to the condition being diagnosed.

The output of the models (e.g., the predictions/suggestions generated via the models) are then relayed to the inferencing service 234, which in turn outputs pre-computed predictions for the current exam that may be sent to the PACS 224. For example, once a diagnostic imaging session is complete and the diagnostic images have been sent to the PACS 224, the predictions may be determined for some or all of the exam parameters, such as the workflow, toolset, and priors. When the user selects the exam (e.g., from a menu of outstanding exams presented in a graphical user interface displayed on a display device of the viewer 236), the exam and pre-computed predictions are displayed to the user automatically via the viewer 236. In other words, when an exam is created at the PACS 224, the inferencing service 234 may receive the suggestions and predictions from each of the models and may assemble a workflow based on the output from the models, including determining which aspects of the suggestions and predictions to include in the workflow for the exam, as well as customizing the suggestions and predictions into the workflow based on known user preferences, known patient information, etc. When the exam is initiated, the images to be analyzed are displayed in a graphical user interface that is formatted according to the workflow and the priors and toolsets are selected and displayed according to the workflow as determined by the output of the models and the inferencing service 234. Further, the viewer 236 may send requests and/or information pertaining to on-demand predictions to the inferencing service 234 during the exam. For example, in response to a user request or once the exam has reached a particular stage of the workflow, the output from the findings model may be fetched and displayed. In this way, the most relevant findings from past exams may be retrieved once the clinician has a better sense of the suspected patient condition (e.g., once some diagnostic indicators have been identified in the images, for example). Likewise, relevant references from the references model may be retrieved in response to user request or once the exam has reached a particular stage of the workflow.

The models 307 may be updated based on data collected during the diagnostic exam. For example, a feedback engine 330 may be configured to monitor the settings selected by the user when performing the exam. The settings may include the suggested/applied workflow and any modifications made to the workflow by the user, whether or not the user opted to view the suggested priors, findings, and/or references (or whether the user selected additional or alternative priors, findings, and/or references to view), which tools from the toolset the user interacted with (and whether the user added any additional or alternative tools), and so forth. The feedback engine 330 may monitor the toolsets selected by the user, the hanging protocol selected by the user (or suggested to the user), as well as the references selected by the user.

Further, the feedback engine 330 may store follow-up data indicative of how effective and/or accurate each assembled workflow is at facilitating a diagnoses of a patient condition. For example, when a workflow is generated by the inferencing service 234 based on output from the models 307, the workflow may be classified by various exam parameters, such as imaging modality, diagnostic goal, and anatomical features imaged. As an example, a first workflow may be classified as a CT workflow for detecting a lesion in a breast, while a second workflow may be classified as an MRI workflow for monitoring brain bleeding in a pediatric patient. After the exams associated with each workflow are performed, the findings/diagnostic assessment saved by the clinician in the exam may be corroborated or not corroborated by another clinician, additional diagnostic testing (e.g., a pathology examination of a biopsied region, a different diagnostic exam with a different imaging modality, etc.), patient symptoms, and/or further clinician-based diagnostic assessments. An indication of whether or not the finding(s) in the exam were corroborated may be stored at the feedback engine along with the other data described above. The follow-up data and indication of corroboration may be used to assign a diagnostic accuracy score to each workflow, when possible, and because each workflow is classified based on exam parameters, the feedback engine may be configured to determine which workflows have relatively high diagnostic accuracy for each different workflow classification. For example, multiple different workflows for detecting a lesion in a breast with CT scanning may be generated, and each may be assigned a diagnostic accuracy score that may be updated as each different workflow is utilized multiple times for different exams. When a high accuracy workflow is identified (e.g., having an accuracy score above a threshold), the high accuracy workflow may be preferentially applied in future breast lesion CT exams, and may be suggested to other medical facilities for breast lesion CT exams, as explained in more detail below with respect to FIG. 4. A similar approach may be taken for exam efficiency, where the duration of the exam may be determined, stored at the feedback engine, and used to rank different workflows based on efficiency (e.g., speed). If a fast workflow is identified for a given classification, without compromising diagnostic accuracy, that workflow may be preferentially applied and/or shared with other facilities.

In some examples, the information stored at the feedback engine 330 may be sent from the feedback engine 330 to the central learning platform to be used as training data 318. Once a threshold amount of feedback data has been collected, the models may be updated/retrained via the training algorithm 308 to update the models 307 stored in the repository 306. Further, in some examples, the feedback engine 330 may be used to locally retrain the models 307 if the models are stored locally at the on-site device(s) 304. For example, different hospitals may have different regulations, preferred workflows, serve different patient demographics, etc., and thus it may be advantageous to train the models in a hospital-specific manner. However, if a particularly optimal workflow is identified at a hospital, the workflow may be shared with other hospitals via the central learning platform.

In this way, the central learning platform 302 may include a plurality of models stored in a repository that may be deployed by one or more on-site computing devices in order to suggest or apply diagnostic workflow settings when a user initiates a diagnostic exam. The workflow settings may include the selection and ordering of action items to be carried out during the exam, the formatting of the graphical user interface used to present the images and other information during the exam, toolsets to be displayed during the exam, prior scans of the patient to be presented during the exam, relevant findings to be presented during the exam, and relevant references to be presented during the exam. The plurality of models may be AI-based models (e.g., machine learning, neural networking, etc.) that are trained using information from prior exams for a plurality of patients. The training data may include, for each patient, relevant clinical data stored at the time of the exam (e.g., blood pressure, heart rate, body temperature, medications, past diagnoses), prior reports/findings (e.g., the findings documented during the exam for the patient, including annotations made to diagnostic images, stored findings, diagnosed conditions), image data (e.g., the images that were acquired and analyzed for the exam), and expert usage data (e.g., corroborated diagnoses as well as workflow information pertaining to the workflow that was applied during the exam, including but not limited to selected priors, selected references, selected toolsets, hanging protocol of images, and the arrangement/display of selected priors, references, and images in viewports).

In some examples, the central learning platform may train the models with training data collected by a single medical facility (e.g., hospital) and only deploy the trained models at the single medical facility. However, in other examples, the central learning platform may draw training data from a plurality of different medical facilities and/or deploy the trained models at a plurality of different medical facilities, as will be explained in more detail below.

The one or more workflow models, such as the models 307 described above, may be stored in the model repository 306 and may be deployed on the central learning platform 302. In such examples, the on-site device(s) may send parameters for an exam to the central learning platform, and the output from the models (e.g., the predictions/suggestions discussed above) may be sent back to the on-site devices where the output may be used by the inferencing service 234 to generate the workflow. In other examples, the models may be stored on and deployed by the on-site device(s) 304, and may be periodically updated when the central learning platform retrains the models and/or may be retrained locally via the feedback engine. In such examples, the inferencing service 234 may supply the exam parameters to the models, and the output from the models may be supplied to the inferencing service 234, as shown in FIG. 3, all within the on-site device(s).

As shown, the inferencing service 234 is stored and executed on the on-site device 304, which may be a server of a medical facility, such as a hospital. The models 307 may stored and executed on the on-site device. Any updates to the models may be provided via notifications sent from the central learning platform, for example. In other examples, the inferencing service 234 is stored and executed on the on-site device, but the models may be trained and updated on the central learning platform. In still further examples, the inferencing service and models may be stored and executed on the central learning platform.

Turning now to FIG. 4, an example integration of the smart engine system of FIG. 3 with multiple healthcare systems is shown. Embodiment 400 shows the central learning platform 302 with the training models repository 306 and a training engine 408 coupled to a plurality of healthcare environments 414, herein hospitals 1 through N. Each hospital may include a plurality of viewers, such as viewers 432. The viewers may be different computing devices utilized by scan technologists, doctors, or other healthcare experts who view and analyze patient images for a suspected condition. Each hospital may further include a smart engine inferencing service 420, which are non-limiting examples of the inferencing service 234 described above, which may generate smart, customized diagnostic exam workflows that may be displayed on the viewers 432. The inferencing service 420 may utilize one or more workflow models trained on the centralized learning platform 302, as discussed above. In some examples, the one or more workflow models may be stored at a smart engine data repository 416. When exams are conducted via the viewers 432, usage data is collected at a user input collection service 418. The usage data includes individual patient data analyzed, toolsets used during the diagnosis, workflows and hanging protocols applied during the diagnosis, as well as the diagnoses delivered by individual healthcare providers at the given hospital and follow-up data (e.g., corroborating the diagnoses or not corroborating the diagnoses). For example, the data may include individual patient data analyzed and diagnoses delivered by multiple healthcare providers at the given hospital, each reviewing the same data. The data and the associated outcomes may be saved in smart engine data repository 416 and used to locally train the models and/or the data and associated outcomes may be communicated to a smart engine training and model update module 408 at the central learning platform so as to update the trained models.

Each hospital may send information (e.g., from the respective smart engine data repositories) to the central learning platform, and the information from each hospital may be used to update the models of the central learning platform. In some examples, the central learning platform 302 may include a common set of models saved in the data repository 306 that may be updated based on information received from all the hospitals, and the models may be deployed to all the hospitals. In doing so, a larger amount of update/training information may be collected, which may improve the accuracy of the models. In other examples, the central learning platform may update the models in a hospital-specific manner, such that information from hospital 1 is only used to update models deployed at hospital 1, information from hospital 2 is only used to update models deployed at hospital 2, etc. In this way, the models may be trained for each medical facility/hospital individually, which may improve the accuracy of the models, particularly if the geographic location or average patient demographics of the hospitals varies considerably. As explained previously, each workflow may be evaluated based on diagnostic accuracy and/or efficiency. When workflows are identified that have a high diagnostic accuracy and/or a high level of efficiency, those workflows may be suggested to all the hospitals, e.g., in the form of a report or notification from the central learning platform. In this way, hospitals may be notified when high accuracy and/or efficiency workflows are developed at other hospitals, and the hospitals may choose to follow some or all of the aspects of the workflows.

Turning now to FIG. 5, an example method 500 for generating a diagnostic exam workflow is shown. The method 500 enables a user at a healthcare environment to be provided with a workflow including toolsets, a hanging protocol, as well as relevant priors and references during an exam of diagnostic images for assisting the user in making a reliable diagnosis of a patient condition based on the diagnostic images. Instructions for carrying out method 500 may be executed by a computing device based on instructions stored on a memory of the computing device, such as the inferencing service 234.

At 502, a notification that diagnostic images have been saved as part of an exam is received. For example, diagnostic images may be acquired with a suitable imaging system, such as the CT imaging system 100 of FIG. 1 and/or imaging system 200 of FIG. 2, and saved in memory of a PACS, such as PACS 224. The images may be saved as part of a diagnostic exam that is to be conducted by a clinician, where the clinician reviews the images and saves any findings determined from the images. The findings may indicate a diagnosed patient condition (such as presence or absence of a tumor), rule out suspected patient conditions, indicate treatment progression, or other medically relevant indications. To conduct the diagnostic exam, the clinician may analyze the acquired images and may choose to compare the images to prior images of the patient acquired during prior imaging scans, reference images of normal tissue, and/or exams of other patients having the same or similar suspected patient conditions (e.g., reasons for the exam being conducted). The clinician may also choose to adjust the diagnostic images while viewing the images, such as by zooming in or out, adjusting contrast of the images, applying image processing/analysis filters (e.g., background removal, vessel highlighting, blood flow analysis, etc.). Further, the clinician may choose to consult previously published/prepared literature related to any suspected patient conditions or imaged anatomical features. In doing so, the accuracy of the findings may be increased. However, selecting relevant prior imaging scans, reference images, prior related exams, reference literature, desired toolsets for performing desired image adjustments, etc., may be time consuming. Further, the clinician may not be aware of all available resources, particularly available prior exams and reference literature. Further still, all of the selections and adjustments discussed above may increase a cognitive load on the clinician, which may increase clinician fatigue and likelihood to make a misdiagnosis.

Thus, one or more aspects of the exam, such as display format of the exam (where certain images/information are displayed), displayed toolsets, and displayed additional information, may be selected automatically and without explicit user input by relying on artificial intelligence-based models trained to predict which prior imaging scans, exams, reports, findings, reference images, reference literature, toolsets, etc., should be presented to the clinician during the exam. The predictions may be based on parameters of the current exam. Accordingly, at 504, method 500 includes identifying parameters associated with the exam. The identified parameters may include, for example, an imaging modality 505 used to acquire the images to be analyzed in the exam, such as whether the images were acquired via CT, ultrasound, MRI, etc. As another example, the body part or region 506 that was scanned is identified (e.g., breast, head, thorax, abdomen, etc.). As yet another example, the diagnostic goal 507 of the exam is determined (e.g., mammogram, lesion detection, tumor progression, concussion, etc.). As a further example, the clinician performing the exam is determined at 508. The clinician may be determined based on information obtained from an electronic medical record of the patient, the exam may be automatically assigned to the clinician (e.g., based on preset rules), or the clinician may be determined when the exam is actually conducted. The parameters associated with the exam may be identified based on information received from the PACS, for example.

At 510, a workflow is generated for conducting the exam, which includes selecting toolsets and priors to be displayed as part of the exam. As explained above with respect to FIG. 3, the workflow may include selection of and/or ordering of action items to be conducted in order to carry out the exam, and the workflow may include which selected information (e.g., priors, references, etc.) are to be displayed, where they are to be displayed, the formatting of the graphical user interface used to present the diagnostic images and other information during the exam, and so forth. The toolset may be displayed during the exam in order to provide quick access to the tools that are predicted to be used by the clinician when analyzing the images in the exam. Further, the relevant priors may be selected based on the patient and diagnostic goal of the exam, such that any on-relevant imaging scans are not presented. For example, if the exam is a mammography exam, all prior mammograms for the patient may be selected and other non-related scans (such as a knee exam conducted to determine if a meniscus is torn) may not be selected. As explained above, the workflow, toolsets, and/or priors may be selected based on the identified parameters and one or more workflow models (e.g., a workflow inference model, a prior selection model, and a toolset prediction model as explained above with respect to FIG. 3). For example, the identified parameters (e.g., imaging modality used to acquire the images, diagnostic goal of the exam, anatomical features imaged, and clinician conducting the exam) may be entered as input into the one or more models, and the one or more models may output suggestions or predictions for the workflow, toolsets, and priors, which may then be saved as part of the exam. The suggestions or predictions output by the models may be sent to the PACS to be saved as part of the exam.

At 512, user input is received selecting the exam to be performed. For example, the clinician may select the exam from a menu of exams assigned to the clinician. Once the exam is selected, the acquired images, selected priors, and selected toolsets are displayed according to the selected workflow, as indicated at 514. In this way, the predictions/suggestions output by the one or more models may be predetermined when the exam is loaded/first created at the PACS, and then presented to the clinician when the clinician requests that the exam be performed. When the user/clinician performs the exam, the clinician may make adjustments to the workflow, such as moving where certain images, priors, etc., are displayed, adjusting display aspects of the images via selection of tools from the toolsets (e.g., pan, tilt, zoom, contrast, etc.), requesting additional priors or toolsets be displayed, and so forth. To ensure that the smart workflows automatically assembled according to the embodiments disclosed herein are actually assisting the clinicians to increase exam efficiency, user interaction with the workflow/exam is tracked at 516. If the user modifies the workflow or otherwise indicates that the workflow, priors, and/or toolsets (or as will be explained below, the findings and/or references) are not adequate or sufficient, this information may be stored and used to re-train the models.

At 518, method 500 determines if findings and/or references have been requested. The findings and/or references may be requested by the user, or the findings and/or references may be requested by the workflow automatically. For example, once the clinician has progressed to a certain stage of the workflow (e.g., entering preliminary findings, identifying particular anatomical features or abnormalities, etc.), the workflow may trigger a request to obtain the findings and/or references. However, in some examples, the findings and/or references may be obtained at the same time as the workflow, priors, and toolsets, or other suitable time. If findings and/or references have not been requested, method 500 proceeds to 522, which will be explained in more detail below.

If findings and/or references have been requested, method 500 proceeds to 520 select the findings and/or references based on the identified parameters and the one or more models and displays the findings and/or references according to the workflow. For example, the identified parameters may be input into the one or more models (e.g., a findings model and a references model as explained above with respect to FIG. 3), which may output suggested findings and/or references. In some examples, any additional relevant information input by the clinician during the exam (e.g., identified anatomical features or abnormalities, preliminary findings, etc.) may also be used as input to the one or more models. The suggested findings may include findings copied over and/or adapted from other prior exams having similar parameters (e.g., similar diagnostic goal, similar imaging modality, similar preliminary findings or identified anatomical features, etc.). The user may then accept or reject the findings, which may expedite the process of recording the findings in the exam. The references may include images of normal (e.g., non-pathological) anatomical features relevant to the exam and/or literature relevant to the exam. The findings and/or references may be displayed in a viewport(s) indicated by the workflow and/or one or more models.

At 522, method 500 determines if the exam is complete. For example, the user may enter input indicating that the exam is complete, e.g., that all images have been analyzed and that any findings identified by the clinician have been saved. If the exam is not complete, method 500 returns to 514 and continues to display the acquired images, priors, toolsets, findings, and/or references according to the selected workflow, track user interaction with the workflow, and fetch findings and/or references when requested. If the exam is complete, method 500 proceeds to 524 and sends information regarding the tracked user interactions to the central learning platform. For example, the details of the workflow, including the identified parameters, user interactions with the workflow during the exam, final findings, etc., may be saved and sent to the central learning platform. The central learning platform may use the information to fine-tune or retrain the models. Further, in some examples, the information regarding the tracked user interactions, as well as diagnostic accuracy of the workflow (e.g., based on follow-up information confirming or not confirming the initial findings the exam) and/or efficiency of the workflow may be used by the computing device (or another computing device at the same medical facility as the computing device executing method 500) and/or the central learning platform to retrain the models in a facility-specific manner. In this way, the workflows may be generated according to preferred medical facility guidelines/protocols, which may help each facility stay in compliance with appropriate jurisdiction-specific regulations, for example. However, the workflows that are generated, and the diagnostic accuracy and/or efficiency of each workflow, may be analyzed by the central learning platform to help train models that are deployed elsewhere and/or to be suggested to other medical facilities, such that multiple, different workflow optimizations may be performed via the different medical facilities, which help expedite identification of high accuracy and/or efficiency workflows that may then be shared with all the medical facilities. Method 500 then ends.

While method 500 was explained above as displaying the acquired images, priors, toolsets, findings, and/or references, receiving user input selecting an exam, and tracking user interaction with the workflow, it is to be understood that in some examples, the computing device that generates the workflow and selects the priors, toolsets, findings, and/or references may be different than the computing device that displays the images, priors, toolsets, findings, and/or references during the exam. For example, once an exam is selected via a viewer computing device coupled to a PACS computing device, the PACS computing device (e.g., storing and executing the inferencing service) may send the images, priors, toolsets, findings, and/or references to the viewer computing device according the workflow parameters generated by the inferencing service, and the exam may be conducted with the viewer computing device.

Turning to FIG. 6, an example method 600 is shown for training and executing one or more diagnostic workflow models, such as the models discussed above with respect to FIG. 3. Method 600 may be carried out by processor(s) of one or more computing devices that are part of a central learning platform, such as central learning platform 302 of FIG. 3 according to instructions stored on non-transitory memory of the one or more computing devices. At 602, a plurality of training datasets are received. Each training dataset may include clinical data, prior reports, and image data for an exam of a respective patient, as indicated at 604. A suitable number of training datasets may be received, such as 200 or 500 datasets, each corresponding to a different exam for a different patient. The clinical data may include measured/recorded patient parameters at the time of the exam (e.g., vital signs, medications, patient information), the prior reports may include prior imaging scans for the patient, prior diagnostic lab test results, or other clinical findings related to the patient, and the image data may include the diagnostic images acquired and saved as part of the exam for the patient. Each training dataset may further include workflow usage data and parameters for the exam of the respective patient, as indicated at 606. For example, the workflow usage data and parameters for the exam may include the hanging protocol of the images for the exam, the viewport at which each prior, reference image or literature, etc., was displayed, clinical data that was displayed during the exam, tools that were used during the exam, findings recorded in the exam, exam duration, and relevant follow-up information (e.g., confirmed patient diagnoses, confirmed misdiagnoses).

At 608, a workflow inference model, prior selection model, toolset prediction model, findings model, and references model are generated based on the training datasets. The models may take any suitable form depending on the method of machine learning/artificial intelligence being performed. For example, if the models are trained using a random forest learning algorithm, the models may each include decision trees. In another example, if the models are trained using artificial neural networks, the models may each include layers of connected artificial neurons (as shown in FIG. 7 and explained in more detail below). The models may be configured to output predictions or suggestions for subsequent exams, including workflow, priors, findings, toolsets, and references to be displayed during subsequent exams, based on parameters of the exams.

At 610, the models may output predictions/suggestions based on exam parameters, when requested by a user or another computing device in communication with the central learning platform. For example, the models may be deployed by the central learning platform and may send predictions/suggestions to an on-site computing device in communication with a PACS when requested. In other examples, the models may be deployed by the on-site computing device.

At 612, the models may be updated based on received workflow usage data. For example, as explained above, when the predictions/suggestions output by the models are used to format/select a workflow, select priors, select toolsets, select findings, and/or select references to be displayed during an exam, user interaction may be tracked to determine if the user made any modifications to the workflow, such as accepting/rejecting findings, moving around where images/findings/references are displayed, searching for different priors or references, etc. Any of these interactions may indicate the predictions/suggestions were not optimal, and thus may be used to re-train the models. Further, in some examples, the diagnostic accuracy of a given set of predictions/suggestions may be calculated based on whether the findings submitted by the clinician in the exam were corroborated, and the models may be trained based on the diagnostic accuracy (e.g., such that the diagnostic accuracy is increased over time). Further still, the exam duration of a given set of predictions/suggestions may be determined and the models may be trained based on the exam duration (e.g., such that the exam duration is decreased over time).

In some examples, as indicated at 614, notifications may be generated and sent to the medical facilities in communication with the learning platform indicating high accuracy and/or high efficiency workflows. As explained previously, when a high accuracy workflow is generated for a given workflow classification (e.g., CT breast lesion), the parameters of that workflow (e.g., how the images are presented, which toolsets were presented, which priors were used, and which references were used) may be included in a notification sent to a respective device at each medical facility. The inferencing service or other administrative group at the medial facility may then choose whether those parameters may be incorporated into the workflows/models at that medical facility. Method 600 then ends.

In this way, various aspects of a diagnostic exam/study may be learned in order to increase diagnostic accuracy and decrease exam time. For example, toolsets used in more optimal workflows are learned as well as their relative positions on an interface. As another example, a hanging protocol of the current scan relative to prior patient scans and references may be learned. As yet another example, an order of action items to be performed during the workflow may be learned.

FIG. 7 shows an example flow 700 of data through the smart engine of FIGS. 3-4 in accordance with the methods of FIGS. 5-6. The data flow enables diagnostic workflows to be learned as a function of their diagnostic efficiency, exam efficiency, reduction of user modification to the exams, etc. A workflow can then be generated and loaded for a user reviewing a patient exam at the time of a diagnosis.

At 702, a variety of inputs are provided to the smart engine (that is, a computing device configured for training and/or executing the models discussed herein). The inputs received at the computing device include clinical data, prior reports, prior imaging data, and experts' usage data. In one example, the data is sourced and saved at a local healthcare environment. For example, the inputs may be patient clinical data for all patients at a given hospital, their prior imaging data, as well as references and expert usage data (such as comments on a diagnosis, a degree of development of a suspected condition, etc., for each of a plurality of exams as well as workflow interface interaction during the exams) from experts at that location. The imaging data may be sourced from imaging systems at the hospital. The data collected at a given location may be saved in a central PACs at the hospital as well as at a central data repository on a server. From there, the data can be retrieved at a smart engine on a central learning platform on a cloud network. Likewise, data may be collected from multiple hospitals communicatively coupled to the cloud network.

At 704, data processing may be performed using machine learning and artificial intelligence algorithm and models at the smart engine. In particular, the inputs received (at 702) from the various healthcare environments may be used to make predictions regarding workflow inferences, prior selections, toolset predictions, and identification of relevant findings and references. For example, the models may analyze each patient scan and the associated diagnosis. Therein, the priors selected by a clinician at the time of making a diagnosis may be monitored. In addition, the toolsets used by the clinician, including the specific tools used, and their positioning relative to the images, may be learned. Further, the diagnosis made by the clinician may be learned and compared to expert usage data to learn if the initial diagnosis was corroborated or not. If the initial diagnosis was corroborated, the model may learn the workflow as a function of the condition, the imaging modality, the clinician identity, the healthcare environment and other such parameters. Learning the workflow includes learning the order in which scans are analyzed, the particular tools that were used in the diagnosis, the specific references that were used in confirming the diagnosis, etc.

At 706, the learning performed at 704 is used to automatically generate and display to a user an optimized workflow. The user herein may be a clinician such as a radiologist and the workflow is generated at least in part responsive to a set of diagnostic images acquired on a patient being saved, as a diagnostic exam, in a storage system such as a PACS. In other examples, the workflow may be generated responsive to the user retrieving a patient diagnostic exam on a display device for diagnosis of a suspected condition. The optimized workflow may be generated based on a set of predictions/suggestions for the workflow, workflow interface, and information to be presented during the exam, where the set of predictions/suggestions may be generated by the central learning platform on the cloud network or locally, such as at the PACS of the given healthcare environment where the scan was performed. The optimized workflow may be displayed on a workflow interface. The workflow may include an optimized order of action items to be performed during the diagnosis. For example, the optimized workflow may include step-by-step instructions that the user can go through to perform a reliable diagnosis. The optimized workflow may also include links to relevant reference images.

Thus, a smart engine (e.g., the central learning platform) may train one or more workflow models that may be deployed to predict or suggest diagnostic exam workflow parameters. The models may be trained by the inputs described above, which may include, for a given past diagnostic exam, the parameters of the exam, patient imaging history (priors), patient clinical data (present and past), patient personal data (age, ailment, ailment history, etc.), and prior reports/diagnoses. The inputs may also include various tools used by the user (e.g., clinician) when the user carried out the exam (e.g., which user interface tools, such as pan, zoom, window-leveling, etc., were selected by the user when carrying out the exam), the different steps of hanging (e.g., displaying) relevant images during the exam, and the different priors that were displayed for comparison during the exam. The same or similar inputs for a plurality of past diagnostic exams may be used to train the models.

Then, when a new exam is conducted, a diagnosis may be made by a clinician based on the imaging data (e.g., the diagnostic medical images acquired by a suitable imaging modality) while also considering the following clinical data for the patient: patient details (sex, age, habits), ailment and history, current/past treatment and medication, results of various clinical tests, etc. The imaging data may be displayed according to a workflow suggested by the one or more models. Further, the clinical data that is presented to the clinician during the exam may be suggested by the one or more models. In this way, similar to how an expert user combines all these facts to make a diagnosis, the smart engine may incorporate all these elements into the system.

FIG. 8 shows an example user interface 800 displayed on a display 802 after selection of a diagnostic exam. For example, user interface 800 may be an example of interface 235 displayed on display device 237 of viewer 236. In particular, the diagnostic exam being carried out via user interface 800 is a digital breast tomosynthesis (DBT) protocol, as shown by the protocol selection menu 804.

Upon selecting the exam and protocol, diagnostic images obtained during the imaging scan (e.g., with CT imaging system 100) may be displayed via user interface 800 according to a workflow generated via suggestions/predictions provided by the one or more models as explained above. For example, a first image 806 and a second image 808 are displayed, according to the workflow. Multiple action items of the workflow are displayed via workflow menu 810. These include steps that the user may follow, and an order in which they need to be followed, for the diagnosis to be performed reliably. The action items of the workflow may include the list of steps predicted by the one or more models. Typically, the user will go through each of the steps to complete the exam. While the smart engine/inferencing service generates the sequence of steps, the menu provides the user the option of changing the sequence of steps. If this happens, feedback regarding the usage and optimize the sequence generation may be saved for later uses. The user may select an individual action item 812 and responsive to the selection, the images to be displayed at that action item are displayed. In some examples, a notification (not shown) may pop-up which displays the details of the action item, such as tools to use, areas to zoom on, features to look for in the image, etc. As shown, the individual action item 812 that has been selected dictates that craniocaudal (CC) and mediolateral oblique (MLO) views of the breast taken with a conventional digital mammography system be shown, and hence the first image 806 and the second image 808 are displayed, which show the breast in the CC and MLO views, respectively. As the use progresses through the exam, DBT images may be shown (CC and MLO views side-by-side and individually), digital mammography images may be shown, etc.

The user may transition through the different steps of the workflow by actuating a workflow icon 814. This allows the user to move through a guided workflow. The user may also navigate through prior studies by actuating a priors icon 816. Actuation of the priors icon may result in the workflow interface being loaded with prior breast scans of the same patient that were already identified as most relevant by the one or more models, as well as reference images that suggested by the one or more models.

FIG. 9 shows an example demonstration of relevant priors selected by the one or more models described herein (e.g., prior selection model 322 of FIG. 3). When a user such as a clinician is performing an exam of a patient, traditionally the user would be forced to navigate to a prior selection page 902 where all prior imaging scans performed on the patient are listed. While an exam selector feature may allow the scans to be filtered by modality (e.g., MRI, ultrasound, CT, etc.), the clinician may still have to sort through a plurality of related and non-related scans and then manually select which scans are relevant and thus should be viewed while conducting the current exam (shown at 904). The one or more models described herein, such as the prior selection model 322, may be trained to automatically determine which prior scans of the scans listed on the prior selection page 902 are relevant to the current exam and identify the scans to be included in the workflow of the exam. For example, the prior scans identified by the prior selection model 322 may be included in one or more viewports of the exam. As used herein, a viewport may refer to a display area of an interface. For example, the exam shown at 904 may include 11 viewports, such as first viewport 906 (where a page of a reference literature relevant to the exam is displayed). The identified relevant prior scans are the scans bounded by the boxes, such as box 908. For example, the most recent scan for the patient, the bone density scan conducted on Dec. 27, 2016, is not identified as relevant to the current exam, as the current exam is a digital mammography exam. The scans in box 908 are both digital mammography scans, and thus are identified as being relevant scans.

FIG. 10 shows an example workflow interface 1000 on a display 802. Herein, the smart engine has suggested relevant reference images for viewing by the user during an exam. In particular, the exam workflow displayed via interface 1000 includes a group of current patient images 1002 and a group of reference images 1004. The current patient images 1002 may be arranged in a defined order for viewing in accordance with the suggested workflow. The reference images 1004 may correspond to images of the same anatomy and same orientation as the images shown in the group of current patient images 1002 and further the reference images may also be loaded in the same defined order. In the depicted example, the reference images 1004 are of the anatomy without disease so as to give the user a basis for comparison and reading. However, in other examples, the reference images may be images of the anatomy with a confirmed presence of the suspected condition and varying degrees of the condition so that the user can compare and assess a progression of the condition. While the depicted example includes reference viewing as part of the reading protocol of the optimized workflow, in other examples, the reference images may be provided as pop-up displays. For example, selection of an image from the group of current patient scans may result in a corresponding reference image to pop-up for comparison. Still other display options are possible.

While not shown, in further examples, additional related literature resources and diagnoses made for similar cases may be retrieved from the database and shown as references.

A technical effect of optimizing the workflow for scan analysis and diagnostics using deep learning techniques is that precision health can be provided by improving diagnostic outcomes. By enabling a computing device to automatically search through patient data and load results by factoring in various aspects of patients' data along with experts' usage and inferences from similar studies and workflows, reliability of diagnoses is improved while reducing the cognitive load and fatigue on a user (such as a radiologist). By leveraging AI algorithms to search through the data, multi-factorial, computation heavy analyses can be performed more accurately, enabling potential issues to be identified that would have otherwise been missed. Further, by sharing workflows at a central learning platform, best-in-class reading protocols and practices can be available to all users across a range of healthcare environments. Further, unwanted user actions can be removed, improving productivity.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
automatically identifying one or more exam parameters associated with a diagnostic exam that includes one or more medical images;
automatically generating a workflow for analyzing the one or more medical images, the workflow including one or more of a diagnostic protocol, a toolset, a prior imaging scan, a prior finding, and a reference image, wherein the workflow is generated based on the one or more exam parameters and wherein the toolset comprises at least one user interface menu option or at least one control button that, when selected, allows a task to be performed;
training an artificial intelligence-based model to predict which of one or more viewports of a user interface are to display the prior imaging scan, the toolset, or the reference image, wherein the training includes training the artificial intelligence-based model using the prior imaging scan, the toolset used by a clinician when making a diagnosis using the prior imaging scan, a relative positioning of one or more tools of the toolset when making the diagnosis, and corroboration of the diagnosis with expert usage data;
automatically executing the artificial intelligence-based model, based at least in part on an imaging modality used to acquire the reference image and without explicit user input, to predict which of the one or more viewports of the user interface are to display the prior imaging scan, the toolset, or the reference image;

displaying the workflow in the predicted one or more viewports of the user interface, wherein a size of the one or more viewports or a position of the one or more viewports is predicted based at least in part on the prior imaging scan, the toolset, the reference image, or a combination thereof; and displaying the one or more medical images in the user interface that is formatted according to the workflow.

2. The method of claim 1, wherein the one or more exam parameters comprise one or more of the imaging modality used to acquire the one or more medical images, a diagnostic goal of the diagnostic exam, anatomical features imaged in the one or more medical images, patient information of a patient imaged in the one or more medical images, and an identity of the clinician performing the diagnostic exam.

3. The method of claim 1, further comprising collecting follow-up data after completion of the diagnostic exam confirming or not confirming one or more findings saved with the diagnostic exam, the follow-up data usable to determine a diagnostic accuracy of the generated workflow.

4. The method of claim 1, wherein the diagnostic protocol includes a list of action items to be performed during the diagnostic exam.

5. The method of claim 1, wherein the workflow further includes a format of a workflow interface via which the one or more medical images, the toolset, the prior imaging scan, the prior finding, and the reference image are displayed.

6. The method of claim 1, wherein automatically generating the workflow comprises automatically generating the workflow according to a set of suggested workflow parameters output by one or more workflow models.

7. The method of claim 6, wherein the one or more workflow models are trained to correlate the one or more exam parameters with the set of suggested workflow parameters based on training datasets that include, for each of a plurality of prior diagnostic exams associated with different respective patients, patient clinical data, prior reports, image data, and diagnostic exam workflow usage data.

8. The method of claim 7, further comprising collecting user interaction data during execution of the diagnostic exam via the generated workflow, the user interaction data usable to retrain the one or more workflow models.

9. A system, comprising:
a storage system; and
a computing device storing instructions executable by a processor of the computing device to:
automatically identify one or more exam parameters associated with a diagnostic exam that includes one or more medical images, the diagnostic exam and the one or more medical images stored in the storage system;
automatically generate a workflow for analyzing the one or more medical images, the workflow including one or more of a diagnostic protocol, a toolset, a prior imaging scan, a prior finding, and a reference image, wherein the workflow is generated based on the one or more exam parameters and wherein the toolset comprises at least one user interface menu option or at least one control button that, when selected, allows a task to be performed;
train an artificial intelligence-based model to predict which of one or more viewports of a user interface are to display the prior imaging scan, the toolset, or the reference image, wherein the training includes training the artificial intelligence-based model using the prior imaging scan, the toolset used by a clinician when making a diagnosis using the prior imaging scan, a relative positioning of one or more tools of the toolset when making the diagnosis, and corroboration of the diagnosis with expert usage; automatically execute the artificial intelligence-based model, based at least in part on an imaging modality used to acquire the reference image and without explicit user input, to predict which of the one or more viewports of the user interface are to display the prior imaging scan, the toolset, or the reference image;

display the workflow in the predicted one or more viewports of the user interface, wherein a size of the one or more viewports or a position of the one or more viewports is predicted based at least in part on the prior imaging scan, the toolset, the reference image, or a combination thereof;

display the one or more medical images in the user interface that is formatted according to the workflow; and send the workflow to the storage system for storage with the one or more medical images as part of the diagnostic exam.

10. The system of claim 9, wherein the workflow comprises predicting a hanging protocol that indicates an order of presentation of the one or more medical images during the diagnostic exam.

11. The system of claim 9, further comprising a viewer including a display device, and wherein the viewer is configured to send a request to the storage system to retrieve the diagnostic exam including the one or more medical images and the workflow, and display via the display device the one or more medical images according to the diagnostic protocol of the workflow and display the toolset, the prior imaging scan, the prior finding, and/or the reference image according to the workflow.

12. The system of claim 9, wherein the one or more exam parameters comprise one or more of the imaging modality used to acquire the one or more medical images, a diagnostic goal of the diagnostic exam, anatomical features imaged in the one or more medical images, patient information of a patient imaged in the one or more medical images, and an identity of the clinician performing the diagnostic exam.

13. The system of claim 9, wherein the diagnostic protocol includes a list of action items to be performed during the diagnostic exam and wherein the workflow further includes a format of a workflow interface via which the one or more medical images, the toolset, the prior imaging scan, the prior finding, and the reference image are displayed.

14. The system of claim 9, wherein automatically generating the workflow comprises automatically generating the workflow according to a set of suggested workflow parameters output by one or more workflow models.

15. The system of claim 14, wherein the one or more workflow models are trained to correlate the one or more exam parameters with the set of suggested workflow parameters based on training datasets that include, for each of a plurality of prior diagnostic exams associated with different respective patients, patient clinical data, prior reports, image data, and diagnostic exam workflow usage data.

16. The system of claim 15, wherein the instructions are executable to:

collect user interaction data during execution of the diagnostic exam via the generated workflow, the user interaction data usable to retrain the one or more workflow models; and collect follow-up data after completion of the diagnostic exam confirming or not confirming one or more findings saved with the diagnostic exam, the follow-up data usable to determine a diagnostic accuracy of the generated workflow.

* * * * *